(12) United States Patent
Buerchner et al.

(10) Patent No.: US 10,973,547 B1
(45) Date of Patent: Apr. 13, 2021

(54) SELF-RETAINING VAGINAL RETRACTOR

(71) Applicant: Birch Concepts, LLC, Menlo Park, CA (US)

(72) Inventors: Catherine Ann Buerchner, San Diego, CA (US); Michael Josef Buerchner, Menlo Park, CA (US)

(73) Assignee: Birch Concepts LLC, Menlo Park, CA (US)

( * ) Notice: Subject to any disclaimer, the term of this patent is extended or adjusted under 35 U.S.C. 154(b) by 177 days.

(21) Appl. No.: 16/267,698

(22) Filed: Feb. 5, 2019

Related U.S. Application Data (60) Provisional application No. 62/630,526, filed on Feb. 14, 2018.

(51) Int. Cl.
| | | |
|---|---|---|
| *A61B 17/42* | (2006.01) | |
| *A61B 17/02* | (2006.01) | |
| A61B 17/00 | (2006.01) | |
| B29L 31/00 | (2006.01) | |
| B29C 41/02 | (2006.01) | |
| B29K 105/00 | (2006.01) | |

(52) U.S. Cl.
CPC .......... *A61B 17/42* (2013.01); *A61B 17/0218* (2013.01); *A61B 2017/00526* (2013.01); *A61B 2017/00862* (2013.01); *A61B 2017/0225* (2013.01); *B29C 41/02* (2013.01); *B29K 2105/0002* (2013.01); *B29L 2031/7546* (2013.01)

(58) Field of Classification Search
CPC ..... A61B 17/42; A61B 17/02; A61B 17/0206; A61B 17/0218; A61B 1/303; A61B 1/32
See application file for complete search history.

(56) References Cited

U.S. PATENT DOCUMENTS

| | | | | |
|---|---|---|---|---|
| 3,841,318 A | * | 10/1974 | Olson | A61B 1/32 600/220 |
| 5,342,385 A | * | 8/1994 | Norelli | A61B 17/02 604/104 |
| 8,864,660 B1 | * | 10/2014 | Yufa | A61B 17/02 600/224 |
| 2017/0281149 A1 | * | 10/2017 | Rolfes | A61B 1/32 |

* cited by examiner

*Primary Examiner* — Christopher J Beccia
(74) *Attorney, Agent, or Firm* — Marc P. Schuyler (57) ABSTRACT

This disclosure provides a retractor for use in repairing vaginal tears following birth. The retractor is formed as a sheet of soft rubber, plastic or silicone and is rolled or folded for vaginal insertion; the retractor is resilient so as to provide a spring force which urges the vaginal canal open to a degree that facilities visualization and obstetric repair while avoiding unnecessary strain on the tissues being repaired. An optional flange structure can be provided so as to provide a structure for the surgeon/OB to reposition the retractor in-situ, and also to serve as a stop or retainer to hold the retractor in place. The disclosed retractor is self-retaining, such that both of a surgeon's hands can be freed for other tasks.

17 Claims, 9 Drawing Sheets

SELF-RETAINING VAGINAL RETRACTOR

CROSS-REFERENCE TO RELATED APPLICATIONS

This application claims the benefit of U.S. Provisional Patent Application No. 62/630,526, filed on Feb. 14, 2018 on behalf of first-named inventor Catherine Ann Buerchner for "Self-Retracting Vaginal Retractor;" this provisional application is hereby incorporated by reference.

FIELD

This disclosure provides a device intended to improve the ease and safety of a surgical repair of obstetrical laceration typically resulting from child birth, and associated manufacturing methods and method of use.

BACKGROUND

Obstetrical laceration (or vaginal tearing) is a common result of natural childbirth; as a baby is delivered through a mother's birth canal the vaginal tissue is stretched beyond the point of tearing. A doctor (e.g., a surgeon or "doctor") must surgically repair the tear quickly after the baby is delivered.

For visualization and retraction during this obstetrical laceration repair, there are a number of methods providers currently use.

Very commonly, the doctor uses his or her hands as a means for visualization and retraction, i.e., one hand is used to hold open the area for repair while the other hand is used to perform repair. However, this may limit how repair is performed as it constrains the surgeon's free hand, and there also is risk to the surgeon of needle-stick injury.

The doctor may also use a metal vaginal retractor. With a metal vaginal retractor, the doctor typically requires assistance of another individual to hold the retractor in place and to position/reposition the retractor for optimal visualization. This need for an assistant to hold the retractor may compete with other important roles in the delivery room, or it may require on-hand presence of additional staff. In addition, metal retractors also have edges and prominences that can also cause damage to the sensitive vaginal tissues, either during insertion or manipulation. With some self-retaining metal retractors, e.g., a "Gelpi" retractor, the edges can be sharp and can penetrate the fragile vaginal tissue, potentially causing more tearing and blood loss. Metal retractors of this type are typically relatively expensive, and are non-disposable, i.e., they are sterilized and reused. These retractors can also be excessively rigid, and might not retain tissues under repair in an ideal posture.

None of the currently-used options for obstetrical laceration repair is ideal. What is needed is a device that can be positioned and manipulated by a doctor for visualization and retraction, that is self-retaining (i.e., that does not require assistance from another health-care professional) and that leaves both hands of the doctor free for use in surgery (repair). Ideally, such a device would present greatly reduced risk of damaging sensitive tissues, and could be easily repositioned in a selective manner by the surgeon to visualize/access different walls of the vaginal canal. Ideally still, such a device could be mass produced and would be both disposable and of low-cost. The present invention satisfies these needs and provides further, related advantages.

BRIEF DESCRIPTION OF THE DRAWINGS

Salient features of several of Applicant's embodiments will become more readily appreciated by reference to the following detailed description, when considered in connection with the drawings enclosed herein.

The subject matter defined by the enumerated claims may be better understood by referring to the following detailed description, which should be read in conjunction with the accompanying drawings. This description of one or more particular embodiments, set out below to enable one to build and use various implementations of the technology set forth by the claims, is not intended to limit the enumerated claims, but to exemplify their application. Without limiting the foregoing, this disclosure provides several different examples of a self-retaining vaginal retractor and related methods of manufacture and use. While specific examples are presented, the principles described herein may also be applied to other methods, devices and systems as well.

DETAILED DESCRIPTION

This disclosure provides a self-retaining vaginal retractor and related methods of manufacture and use; embodiments of this retractor will hereafter also be referred to as a "SRVR" or simply a "device." This device provides an aid for a doctor to facilitate better visualization of and quick repair of vaginal lacerations or episiotomies. As the device is self-retaining, it does not require assistance of another health care professional (e.g., nurse or doctor) in order to hold the device in place during surgical repair. The doctor for example can work quickly to suture lacerations with two available hands and without required assistance. In one embodiment, the device can be made from a soft, nonreactive material such as a soft rubber or plastic or silicone; the device therefore presents greatly reduced risk of damage to patient tissues than do conventional metal retractors, because it is relatively soft and flexible, with no sharp edges, and non-reactive. Such a device is also much less expensively manufactured and distributed, and can be easily trimmed or adjusted in-situ, if necessary, to further suit the needs of the doctor and/or the patient, and can be disposable, i.e., substantially eliminating costs associated with sterilization and handling. Finally, incidence of needle sticks are substantially reduced as the doctor does not have to hold the device or take other action to keep the vaginal introitus open with a non-operating hand. The device can also be placed and/or repositioned on demand to a different rotational angle to allow visualization of vaginal sulcus tears, thus enabling more efficient vaginal sulcus tear repairs and reducing blood loss. At the end of any vaginal repairs, the device is easily removed again, with reduced risk of patient or doctor injury.

In some embodiments, such a device is made out of a non-reactive soft plastic, rubber or silicone that will not cause a negative reaction with patient tissues, and is sufficiently pliable such that it both can be folded yet will not further damage lacerated tissues; such a device also advantageously has sufficient structural resiliency that it will provide for visualization, essentially holding the vaginal canal sufficiently open that injured tissue can be more easily accessed and repaired by the doctor. In one embodiment, this resiliency can be facilitated by a rib embedded into (or formed out of) the material to create a spring force to hold the vaginal canal open to the required degree while being sufficiently pliant so as to deform as the tear is repaired (sutured). This spring force (and the thickness/material of the rib) is matched to the typical forces of the tissues under repair, which can be generally consistent for typical patients; as a result, the device conforms to the requirements of most all patients, with in-situ trimming by the doctor providing the only adjustments needed for most patients. The design of the rib (e.g., thickness) can be tailored so as to provide the appropriate spring force given the material properties of the device and given the expected resiliency of the tissues typically at issue, and in some embodiments, the rib can be omitted entirely (e.g., if the sheet material provides the desired resiliency); as a result, suitable material selection and rib (and/or spring force) particulars are implementation choices within the design discretion and capabilities of one having ordinary skill in the art. For example, in an embodiment where the device is designed essentially as a sheet of a soft rubber, the device is partially folded for vaginal insertion and the rib provides a spring force which urges the device to return toward an original form—in such an embodiment, the rib and/or material is designed to provide the right amount of spring force so as to hold the device in place in a stable manner (and provide visualization), but not so much force that it will damage the vaginal tissues. The design also provides a flexible counterforce, such that as repair is effectuated by the doctor, the device can change shape in a flexible manner while continuing to hold the tissues under repair in an optimal posture. As noted, in other embodiments, the rib can be omitted entirely, e.g., with the constituent material of the device itself providing the appropriate spring force and the thickness of the device itself can be varied to create the appropriate spring force. Note that the terms "fold" and "folded" as used herein should be understood to mean bent, plied, rolled, or otherwise deformed, i.e., the term does not require that the sheet be creased or inelastically handled. In yet another embodiment, the retractor is formed so as to carry a "flange" or "stop" that retains the retractor at an appropriate posture relative to vaginal introitus; depending on implementation, this flange can also be used to provide a mechanism for the doctor to grip the retractor and reposition the retractor as needed during a procedure. This flange is also optional, and for some embodiments, the functions of the flange and the rib as described above can be combined in a common structure (or otherwise arranged as multiple structures).

Because the device in one embodiment lacks rigid edges of a metal retractor, e.g., as it is instead configured as a soft plastic, rubber or silicone, it presents greatly reduced risk of causing additional trauma during insertion, manipulation or removal. This device can also be manufactured at a fraction of the cost of metal retractors, and can be molded and/or manufactured in bulk and cut to form individual medical devices. Ideally, the device is distributed in sterilized form, such that it is ready for immediate use once removed from packaging.

Figure 1:
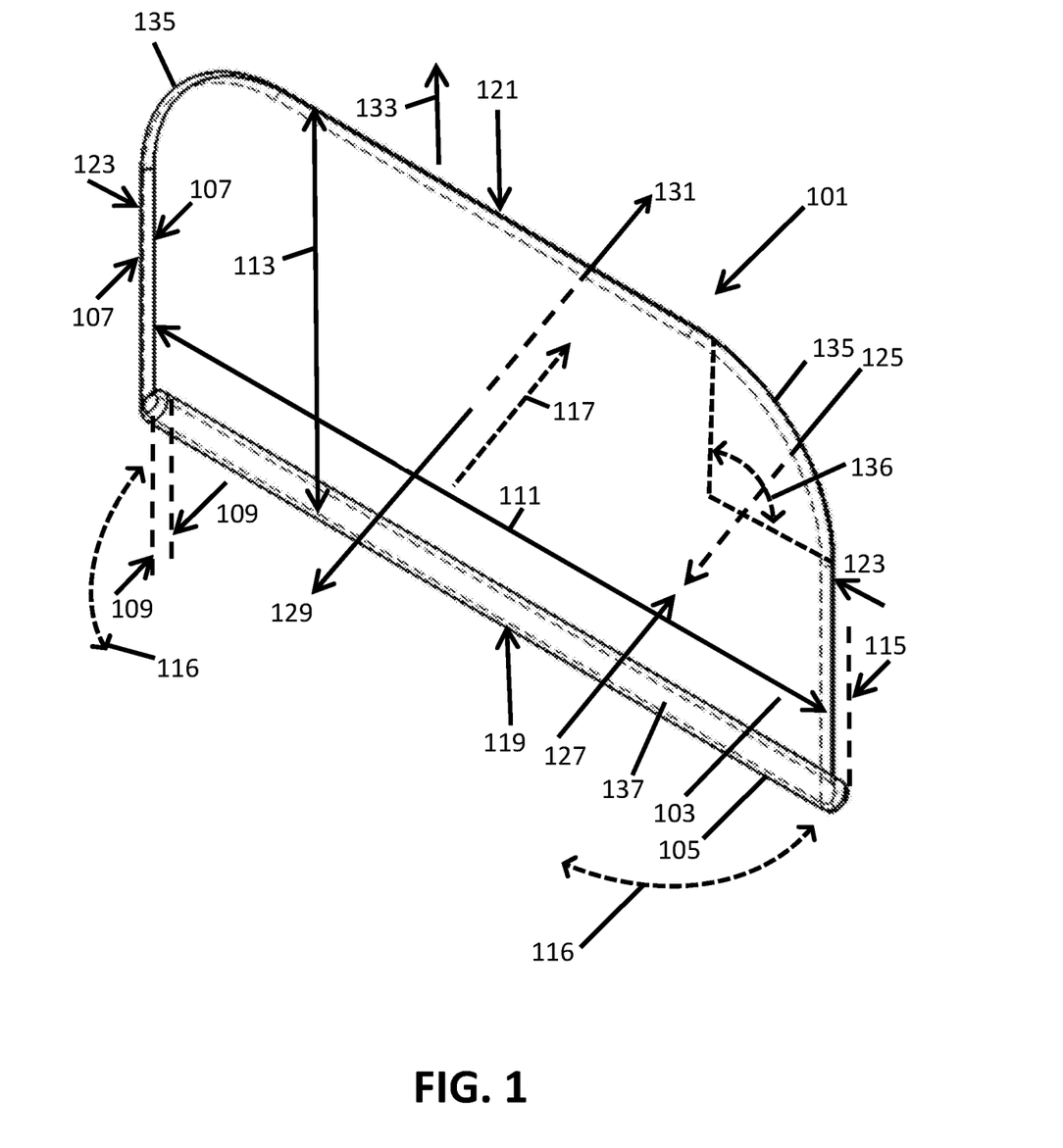
FIG. 1 is a perspective view of one embodiment of a self-retaining vaginal retractor in a native state, that is, unfolded and prior to use.

FIG. 1 shows one exemplary device 101 prior to usage (i.e., removed from protective, sterile packaging), in a "native" state. In the depicted embodiment, the device 101 can be configured as a substantially flat sheet 103 of smooth material, with a rib 105 (as previously mentioned) being used to enhance residency of the material and also provide added structural support. The device has a substantially consistent thickness (generally represented by arrows 107') and the rib is seen to be slightly thicker than general sheet thickness, as designated by a pair of arrows 109. The device also has a width dimension, generally represented by arrowed line 111 and a length dimension, generally represented by arrowed line 113. Typically, the retractor is distributed in a single size only, e.g., with thickness, length and width dimensions of approximately 1.5, 60 and 90 millimeters (mm), respectively; in other implementations however, it is possible to fabricate the retractor in multiple sizes, for example, with a thickness of 1.5 mm and width and length dimensions of 60 mm/80 mm or 70 mm/100 mm, respectively. In one embodiment, the retractor can be made slightly large such that the doctor can trim the retractor in-situ to any desired sizing, on a basis customized for each patient.

As seen in FIG. 1, the rib (or flange) 105 in this embodiment protrudes relative to a flat side 125 of the device, as indicated by numeral 115, and serves to provide a stop during vaginal insertion when the device is deployed. To fold the device into this shape, opposing lateral ends 123 of the device are folded toward each other, in a direction indicated by arrows 116, while a lateral midpoint of the device is moved in the opposite direction, per numeral 117, to roll, bend or "fold" the device for vaginal insertion. Flat side 125 will thus contact vaginal tissue during insertion and face outward (in direction 131), while an opposing flat side 127 will form a concave surface facing radially inward (in direction 129). With the device thus folded, an insertion end 121 of the device (along the length dimension) is inserted into the vagina, in the direction generally designated by numeral 133 (i.e., parallel to the axis along which the device is folded or rolled). As noted earlier, the flange or rib 105 is carried in this embodiment at the opposite longitudinal end 119 of the device along its length dimension. As alluded to earlier, the rib/flange 105 serves a tripartite purpose in this embodiment of (1) providing structure and resiliency, to urge the sheet once deployed to return to its native, flat state (and thus provides a spring force to hold the vaginal introitus open to permit visualization and/or tissue repair), (2) providing a stop that inhibits insertion of the device beyond the position of the rib/flange 105, and (3) it also provides a control structure by which the doctor can reposition the device once inserted, for example, rotating the device around the insertion axis (i.e., around the length dimension 113) and also allow the doctor to grip and easily remove the device after surgery. As noted earlier, in some embodiments, the rib and the flange and their various functions can be separated in to multiple structures, e.g., more than one rib can be used, or a rib and flange/stop can be formed as separate structures or individually omitted.

FIG. 1 also shows some further, optional features, e.g., in one embodiment, the rib can be formed by rolling or bonding a distal end of the sheet of flexible material around a rod or spine 137; in addition, the insertion end of the device 121 can also be tapered in transition to opposing lateral ends 123, such that this transition exhibits a gradual radius of curvature 136) at each of two corners 135 (the radius of curvature 136 is depicted in dashed lines at one corner only). This structure permits the device to be structured to facilitate insertion, for example, by not presenting any corners that might inhibit insertion or cause patient discomfort. The spring force provided by the retractor (e.g., by the material and/or flange and/or rib) urges a return to a native state as seen in FIG. 1, such that when inserted, the device postures the vaginal introitus for repair, and when removed, the device tends to unroll/unfold.

Figure 2A:
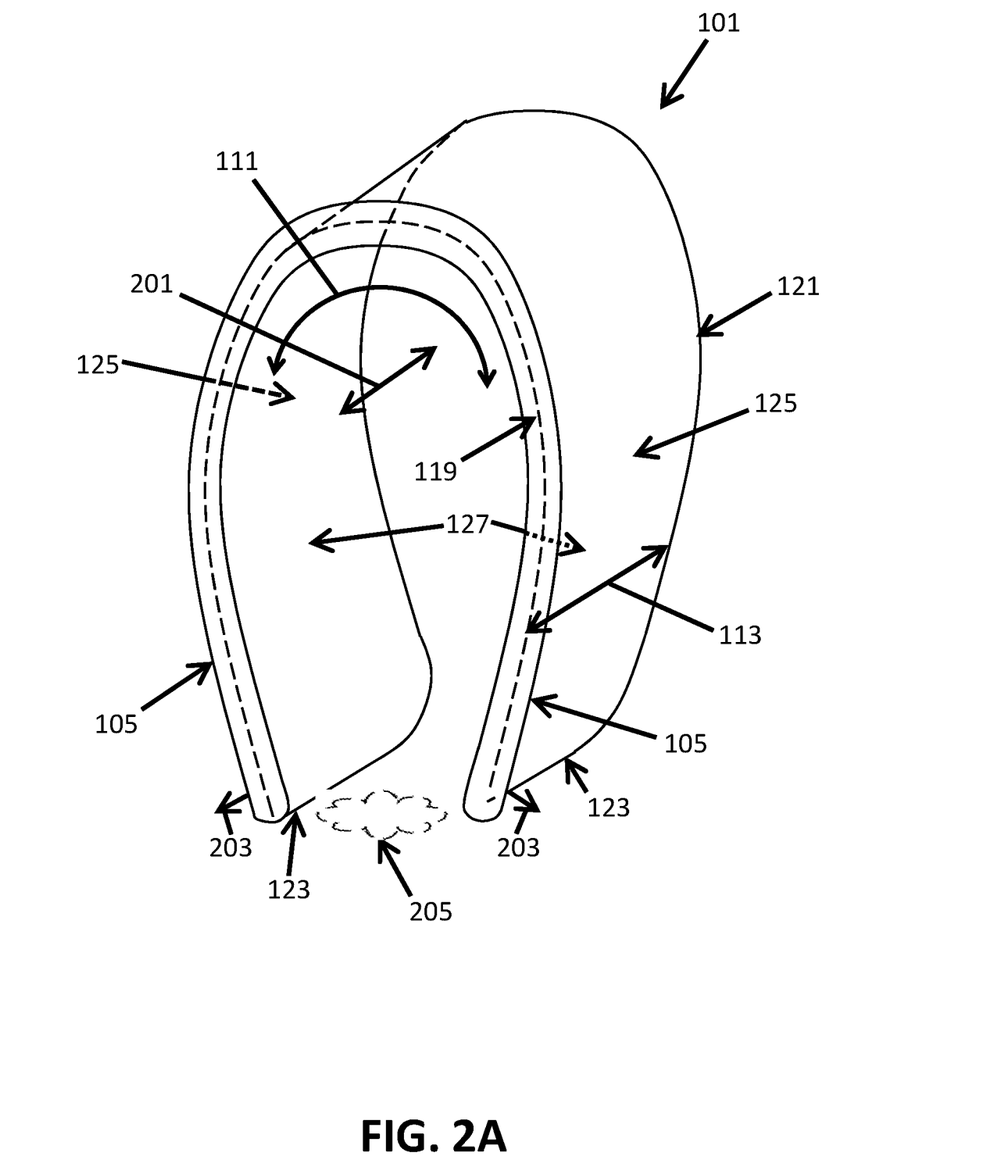
FIG. 2A is an illustrative view of one embodiment of a self-retaining vaginal retractor in a deployed state, that is, where it has been folded and vaginally inserted to permit visualization and/or repair of damaged tissue.

FIG. 2A shows the retractor 101 rolled, bent or "folded" for vaginal insertion. More particular, the device is rolled along its width 111, around axis 201, so as to be inserted and withdrawn generally in the direction indicated by arrow 201. In this configuration, a first longitudinal end 121 is inserted vaginally, while the rib or flange 105 at the opposing end 119 protrudes from the vaginal introitus, with flange 105 facing outwardly (in direction 203) and acting as a radial, externally facing stop. As noted earlier, a first surface of the retractor 125 will face outwardly and contact vaginal tissue, while a second surface 127 faces inwardly toward the center of the vaginal canal. In this configuration, lateral ends 123 are bent toward each other, but the spring force and dimensions of the retractor are such that the ends remain somewhat apart, leaving a region 205 approximately 3-4 centimeters wide for visualization or to expose lacerated tissue of the vaginal wall. It is in this region that the doctor effectuates surgical repair, while rotating the retractor around axis 201 (i.e., rotationally, in direction of arrow 111) so as to visualize any desired region of the vaginal wall.

Figure 2B:
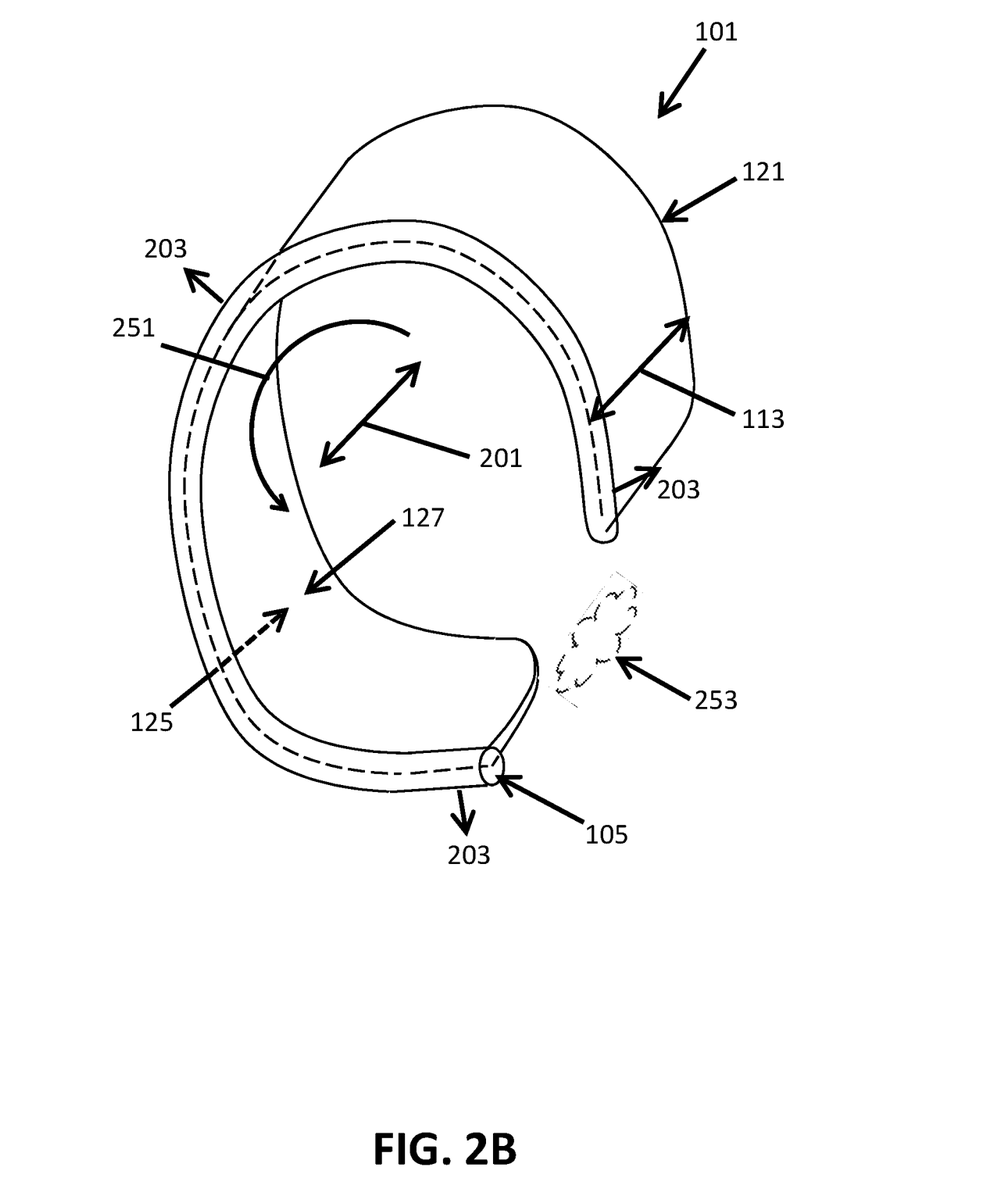
FIG. 2B is another illustrative view of one embodiment of a self-retaining vaginal retractor in a deployed state.

FIG. 2B shows the retractor 101 once again in its deployed or inserted state (i.e., rolled, bent or "folded"). Relative to its depiction in FIG. 2A, it has now been selectively rotated around axis 201, in the direction of arrow 251, so as to provide a doctor with visualization and/or access to another portion of the vaginal wall, represented by reference numeral 253. During a procedure, the doctor can reposition the retractor as many times and to as many orientations as necessary so as to access different tissues as desired or necessary. Once again, the rib or "flange" 105 is seen facing a radially outward direction, so as to provide a stop against surrounding tissues and so as to provide the doctor with a means of repositioning and removing the retractor. As noted earlier, the retractor is typically inexpensively, and is disposed of sanitarily following use.

Figure 3:
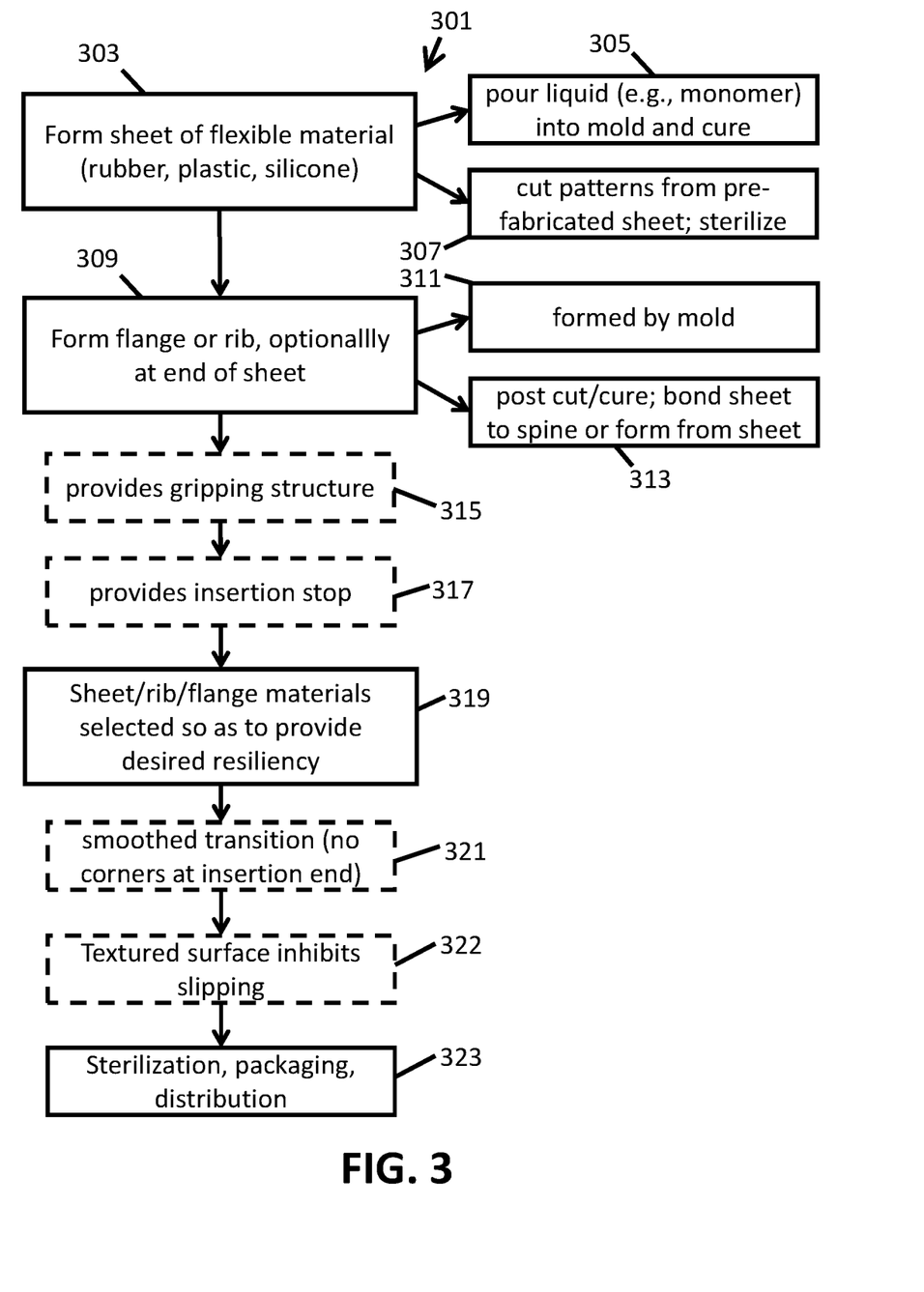
FIG. 3 is a flow-chart showing one embodiment of a method of manufacture of a self-retaining vaginal retractor, such as the one illustrated in FIG. 1 or 2A-2B.

FIG. 3 shows a flow chart associated with one embodiment of a method 301 for manufacturing the retractor. As denoted by numeral 303, a sheet is formed of a flexible soft non-reactionary material, such as a soft rubber, plastic or silicone. Such a material can be poured into a liquid mold as indicated by numeral 305, for example, as a liquid monomer that is then cured so as to form a polymer; this example is non-limiting. In this manner, each retractor can be individually molded, optionally in a manner requiring no further processing (other than cure); for example, the material can be molded so as to have a rib or flange already formed as part of the sheet in a single casting step, per numeral 307. In another embodiment, the device is instead cut from a roll of material (and then an optional rib or flange can be formed for each device following a cutting step), with the device then being sterilized and packaged sterilely or packaged and sterilized in package.

Numeral 309 refers to the formation of an optional flange and/or rib, optionally at one end of the sheet. As indicated by numeral 311, such a rib or flange (or more than one rib or flange) can be formed as part of the molding process. Alternatively, per numeral 313, post cure or cut, one or more ribs or flanges can be formed. For example, as referred to earlier, in one embodiment, a spine of resilient material can be bonded to an end of the sheet, with the sheet being "rolled around" the spine so as to encase it; a heat treatment or other bonding process can be used to permanently finish a rib structure in this manner. As denoted by dashed-line boxes 315 and 317, the flange and/or rib structure, in addition to contributing to the spring force which urges the sheet back to a planar (or "native" state), provides a control surface for gripping/positioning the device, and also provides an insertion stop, inhibiting excessive insertion of the device. Per numeral 319, the spine, and/or rib thickness, in one embodiment are selected so as to provide exactly the "right amount" of spring force to hold the introitus open during a procedure, yet easily deform as tissues are repaired in a manner that does not strain either damaged or repaired tissues. As indicated by numeral 321, the insertion end of the device is optionally curved so as to create no corners or edges that can cause patient discomfort or otherwise inhibit insertion or repositioning of the device. As noted earlier, the material selection also is advantageously made so as to be easily trimmed by the doctor at the time of procedure, so as to provide ready in-situ customization. Selection of the suitable materials and appropriate spring force for the device are a matter of design discretion within the level of ordinary skill in the art. Per numeral 322, an outward facing surface of the retractor (that is, the surface that will directly contact tissue during deployment) can optionally be made to be textured so as to inhibit undesired slipping. Finally, per numeral 323, the device is sterilized and/or packaged and/or distributed for use.

Figure 4:
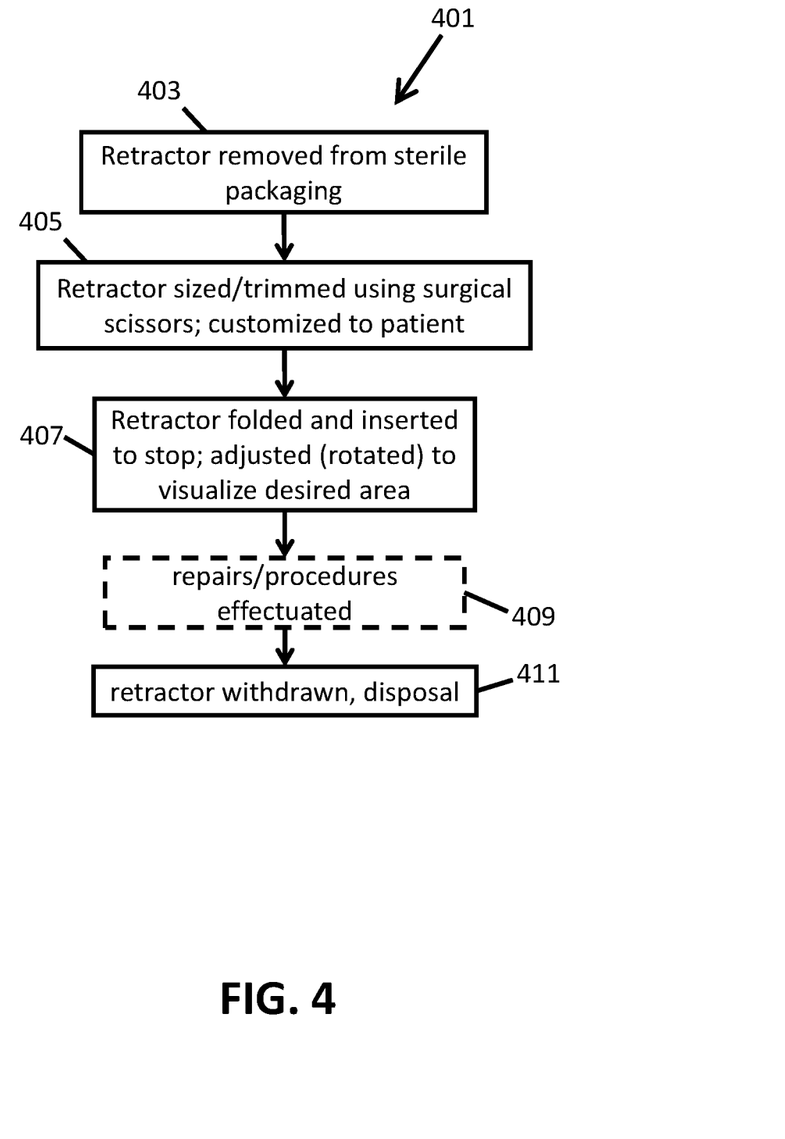
FIG. 4 is a flow-chart showing a method of use of the self-retaining vaginal retractor.

FIG. 4 provides a flow chart 401 relating to exemplary methods of using the device, e.g., during a obstetric procedure. The retractor is removed from individualized, sterilized packaging, per numeral 403. It is then optionally sized or trimmed in-situ (e.g., in the delivery or operating room) using surgical scissors, per numeral 405. Once adjusted as necessary, the retractor is folded for vaginal insertion, and it is inserted approximately to the stop position, that is, with the flange facing radially outward and inserted to a point proximate to external tissues, per numeral 407; the doctor can rotate and/or reposition the device as necessary so as to visualize the desired region of the vaginal wall. Per numeral 409, the doctor optionally then performs repairs of affected tissue, or otherwise performs treatment of the area exposed by the open end of the retractor (that is, at the region between the folded, two opposing lateral sides, such as represented by numerals 205 or 253 in FIGS. 2A and 2B, respectively). Repositioning of the retractor and additional procedures/repairs can be performed as needed. Finally, once the procedure is complete, the retractor is removed and is sanitarily disposed of, per numeral 411.

Returning briefly to FIG. 1, it was earlier mentioned that in one embodiment, one of the opposing flat sides of the sheet of material (i.e., side 125) can be made to be textured so as to inhibit slipping during insertion (i.e., so as to provide a small friction force, to help keep the device in place when inserted into the vaginal cavity during surgery, but also to permit easy removal by the doctor when surgery is completed). FIGS. 5A-5D and 6 are used to provide examples to help illustrate such a design option.

Figure 5A:
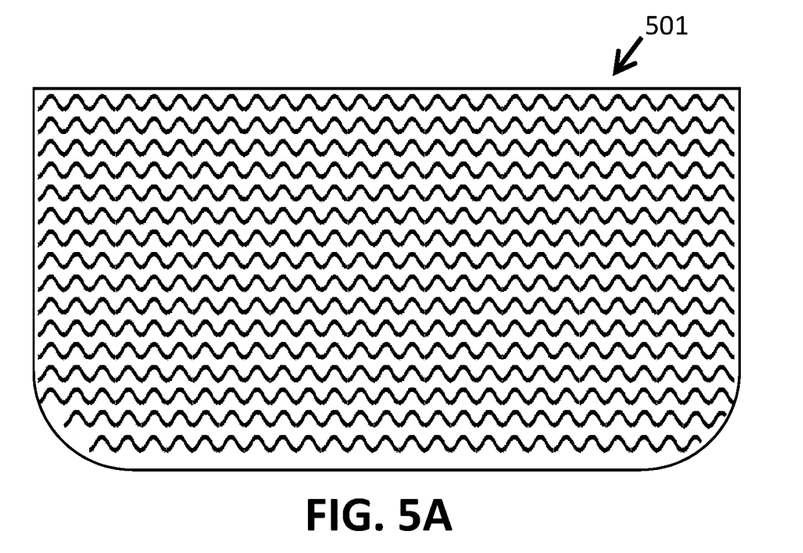
FIGS. 5A, 5B, 5C, and 5D are illustrations of optional surface texture on one surface of the self-retaining vaginal retractor.
Figure 5B:
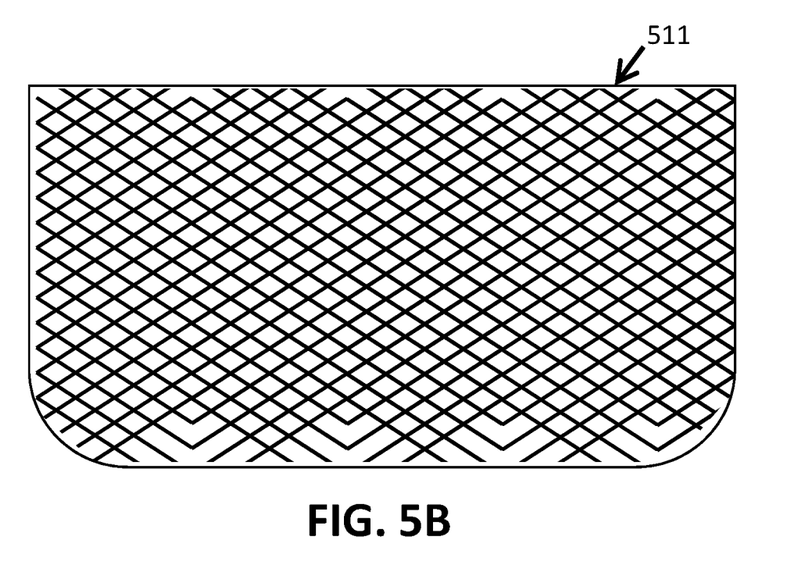
Figure 5C:
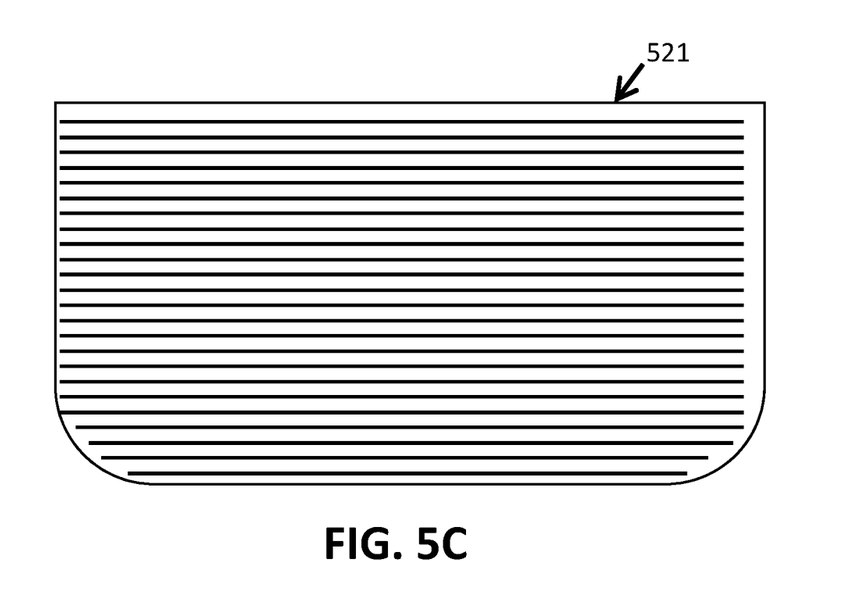
Figure 5D:
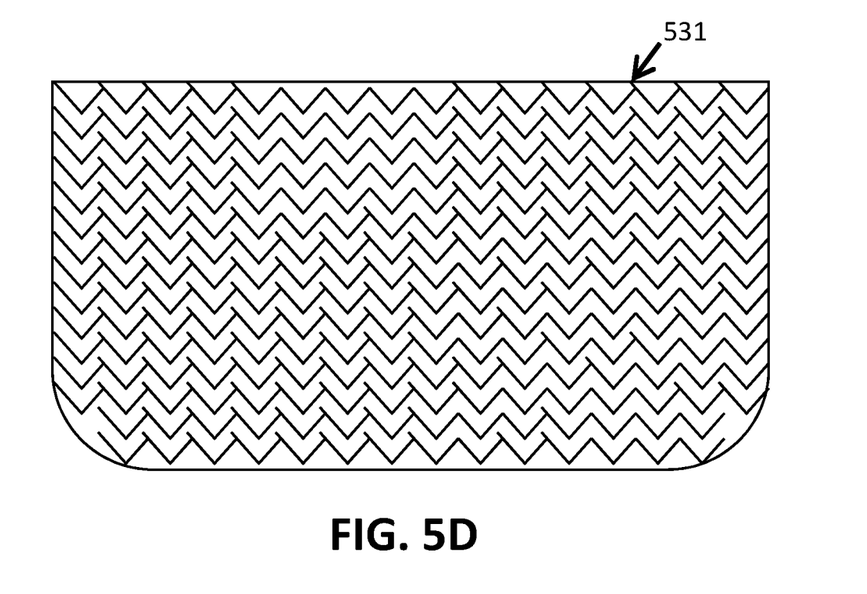

More particularly, FIG. 5A illustrates one embodiment 501 where the texture is in the form of a wavy texture pattern. FIG. 5B illustrates another embodiment 511 where the texture is in the form of a knurled pattern. FIGS. 5C and 5D respective show examples where the texture can be configured as a ridged or herringbone pattern, respectively. Other configurations, patterns and textures will also occur to those having ordinary skill in the art. In general, the amount of texturing which is appropriate is such that the device is not abrasive to tissue (e.g., it does not have excessive surface roughness), but at the same time, inhibits unintended movement. As used here, a "textured surface" refers to any material properties and/or surface roughness and/or surface properties which serve these purposes. Once again, the configuration of any texture is within the design discretion of one having ordinary skill in the art. In one embodiment, this texturing can be formed as part of the mold, such that a molding process can be used to fabricate the device in one step; in other embodiments, the texturing can be created after sheet formation, for example, using a process that heats, scores or deforms an existing sheet. Optionally, the texture if used can be formed so as to be asymmetric, that is, so as to inhibit movement in one direction more than another.

Figure 6:
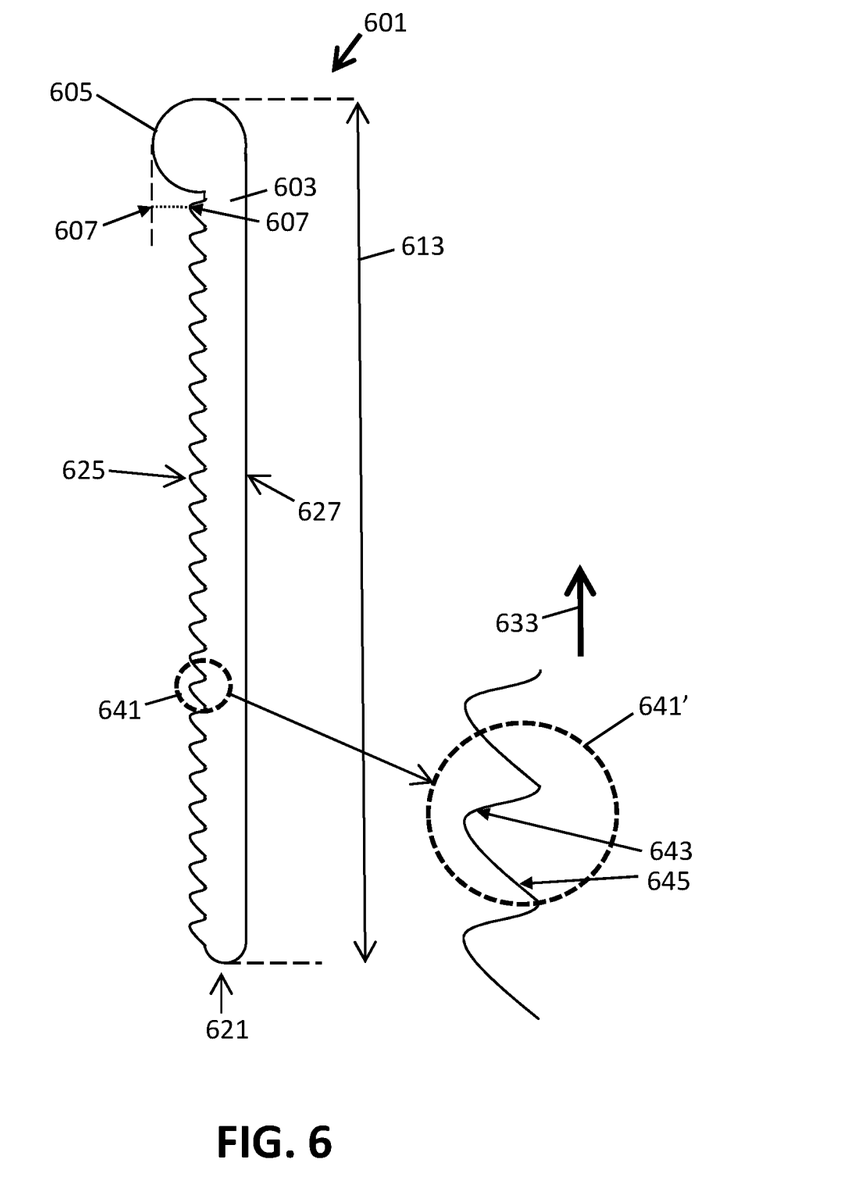
FIG. 6 is a side view of a self-retaining vaginal retractor showing an example of surface texture on one surface of the self-retaining vaginal retractor.

FIG. 6 shows one such embodiment 601. The device is seen once again to have a sheet of material 603 with a rib or flange 605 formed at one end. This flange is raised above an average height of the sheet, as indicated by arrows 607, so as to provide a stop, as referenced earlier. A length dimension of the retractor (which also represents the insertion direction) is generally indicated by numeral 613, with an insertion end of the device being demarked by numeral 621. A first planar side of the device 625, on the same side of the sheet as the flange 605, will contact vaginal tissue during deployment of the device, while a second planar side 627 will face radially inward, toward the center of the vaginal canal during insertion. A small, circular area 641 shows a raised pattern, for example, as was exemplified in FIGS. 5A-5D, and is shown in expanded view at circle 641'. In this embodiment, the texture of the surface is seen to have a slightly steeper slope 643 in a direction toward the flange (i.e., away from the insertion direction), so as to help keep the retractor inserted during a procedure; a second, slightly shallower slope (relative to the planar surface of the sheet) faces the insertion direction, such that the device is slightly easier to insert than to withdraw. In alternative embodiments, these slopes can be symmetrical, or made such that texturing inhibits rotation of the retractor while deployed more than it inhibits insertion/withdrawal, e.g., a steeper slope can be made parallel to the insertion direction. Naturally, many alternatives will occur to those having ordinary skill in the art. It should be understood that dimensions as depicted in FIG. 6 are exaggerated, to assist with illustration and explanation of structure and purpose, with proper dimensioning also being within the level of ordinary skill in the art.

Figure 7:
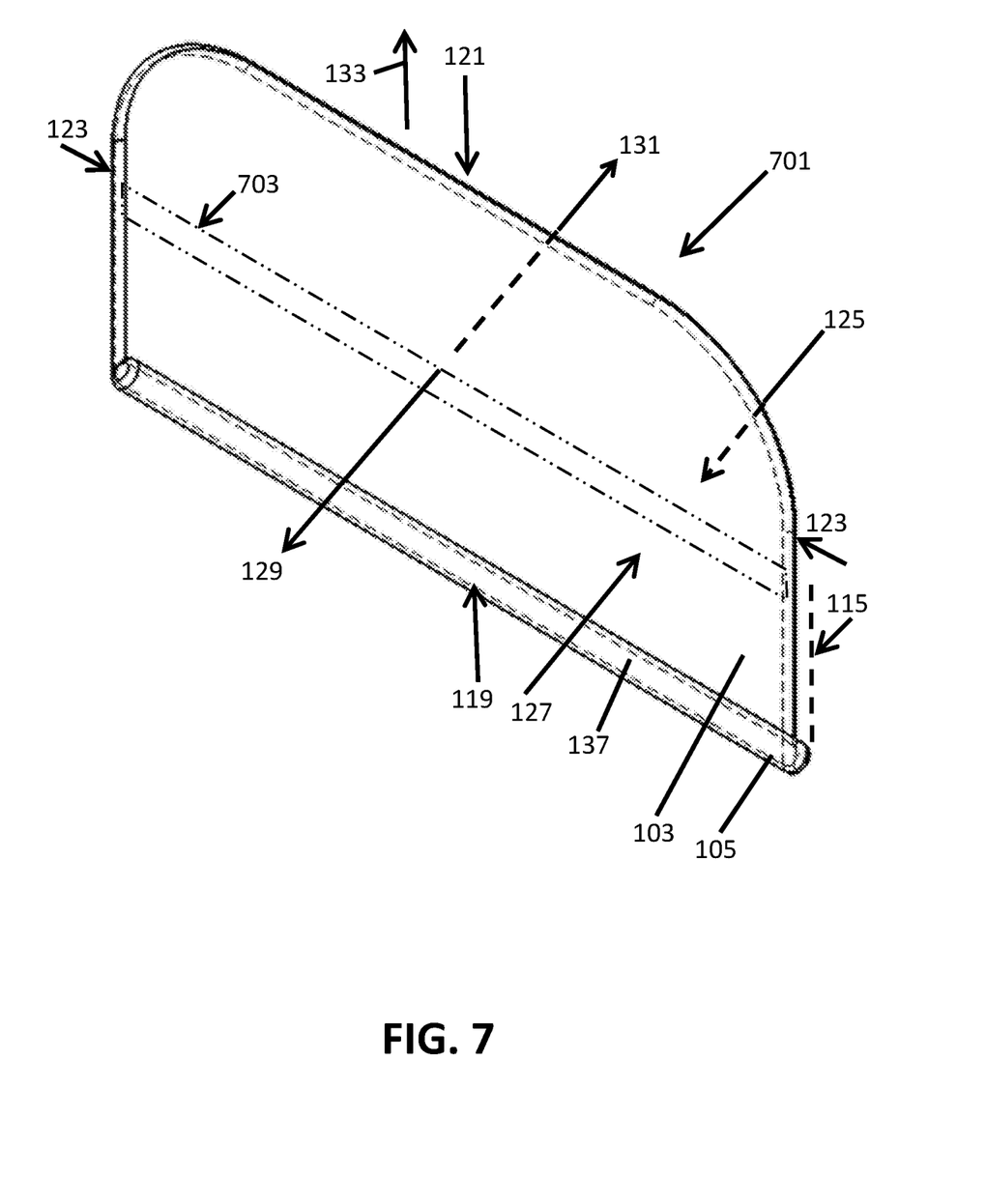
FIG. 7 is a perspective view of one embodiment of a self-retaining vaginal retractor.

FIG. 7 shows an alternative embodiment of a retractor, generally designated by numeral 701. Generally speaking, the configuration of the depicted retractor is similar to that seen in FIG. 1, but in this embodiment, the functions of flange/rib are split. That is to say, the retractor 701 has a flange 105 (as was the case for FIG. 1) but in FIG. 7, a separated rib 703 is also seen at a position intermediate to the length of the device; this rib extends between opposing lateral ends 123, so as to create a substantially uniform spring force throughout the width of the device. Note that as seen in FIG. 7, the rib 703 is substantially flat relative to the plane of the sheet, i.e., such that it creates a spring force but does not impede insertion or withdrawal. These various features are not required for all embodiments, and different configurations will readily occur those having ordinary skill in the art; for example, in other embodiments, ribs can be made asymmetric, non-planar, dimensioned so as to not span device width or in a manner that is longitudinally-oriented, configured as multiple structures, or omitted entirely. In one embodiment, the rib can be made of a second, substantially elastic material which is stiffer than the bulk of the device (i.e., the sheet), so as to provide the desired spring force. Other structural designs are also possible in other embodiments, e.g., to fulfill any of the goals described above in any combination/permutation desired by the doctor or otherwise believed to be advantageous to a particular repair scenario.

The device is preferably sterilized and packaged in a manner where it can be opened easily in the operating/delivery room for one-time customization and/or use, after which the device is disposed of. A variety of manufacturing technologies can be used for device manufacture. For example, in one embodiment, the constituent rubber or plastic or silicone material is poured in a liquid form to form a substantially planar panel of relatively large size; a rib can optionally be formed at each of two opposing ends of this panel as part of the mold, and a cure process can then be used to harden the material relative to its liquid form; alternatively, one or more ribs can be formed by rolling the hardened/cured rubber/plastic or by otherwise adding the rib structure or forming it after device manufacture (e.g., via a heat treatment process). The panel can then be split down the middle and cut into individual products, which are then sterilized, packaged and distributed. Naturally, depending on implementation, these manufacturing steps can be reordered or other steps can be added or substituted. For example, in one possible embodiment, the device can be formed by pouring a liquid monomer, which is then cured (i.e., polymerized) to form a relatively stable structure, which can then be processed in a manner consistent with the foregoing. Other materials, devices and processes can be used to achieve the goals and design features referenced above, and will no doubt occur to those having ordinary skill in the art.

Various alternatives to the foregoing techniques will readily occur to those having skill in the art. Accordingly, the foregoing discussion is intended to be illustrative only; other designs, uses, alternatives, modifications and improvements will also occur to those having skill in the art which are nonetheless within the spirit and scope of the present disclosure, which is limited and defined only by the following claims and equivalents thereto.

We claim:

1. A method of fabricating a retractor for obstetric use, the method comprising:
    forming a sheet of a flexible material, the flexible material comprising at least one of a rubber, plastic or silicone, wherein the sheet has two opposing sides along a width dimension, two opposing ends along a length dimension, and a height dimension;
    wherein forming the sheet further comprises forming a flange at a first one of the two opposing ends, the flange extending between the two opposing sides, the flange providing a structure to grip the sheet, and to position and withdraw the sheet while in a deployed state, wherein the flange is raised along the height dimension relative to a first one of the two opposing sides and in a direction away from a second one of the two opposing sides, so as to provide a stop inhibiting vaginal insertion along the length dimension beyond a position dictated by the flange; and wherein the flexible material and the flange are to permit the sheet to be selectively rolled or folded to urge the flexible material toward the deployed state, to provide a spring force to hold open a vaginal canal for obstetric visualization and to urge the sheet to unroll or unfold to return to a native state.

2. The method of claim 1, wherein forming the sheet comprises pouring a liquid into a mold and curing the liquid to form the flexible material.

3. The method of claim 2, wherein the liquid comprises a monomer and wherein curing the liquid comprises converting the monomer into a polymer.

4. The method of claim 2, wherein the mold is defined so as to impart structures on the first one of the two opposing sides, raised along the height dimension relative to the first one of the two opposing sides and in a direction away from a second one of the two opposing sides, such that the structures are to engage tissue of the vaginal canal during vaginal insertion.

5. The method of claim 4, wherein the first one of the two opposing sides is substantially planar and wherein the structures have a first slope relative to a plane occupied by the first one of the two opposing sides and a second slope relative to the plane occupied by the first one of the two opposing sides, wherein the first slope is steeper than the second slope relative to the plane, and wherein the first slope of the structures faces the flange along the length dimension and the second slope of the structures faces away from the flange along the length dimension.

6. The method of claim 5, wherein the mold is defined so as to impart the flange, such that the forming the flange comprises the pouring of the liquid into the mold and the curing of the liquid.

7. The method of claim 1, wherein forming the sheet of flexible material comprises forming the sheet so as to be cuttable with surgical scissors.

8. The method of claim 1, wherein the first one of the two opposing sides supports structures which are raised along the height dimension relative to the first one of the two opposing sides and in a direction away from a second one of the two opposing sides, such that the structures are to engage tissue of the vaginal canal during vaginal insertion.

9. The method of claim 7, wherein the first one of the two opposing sides is substantially planar and wherein the structures have a first slope relative to a plane occupied by the first one of the two opposing sides and a second slope relative to the plane occupied by the first one of the two opposing sides, wherein the first slope is steeper than the second slope relative to the plane, and wherein the first slope of the structures faces the flange along the length dimension and the second slope of the structures faces away from the flange along the length dimension.

10. The method of claim 1, wherein a second one of the two opposing ends is progressively tapered in transitioning to the two opposing sides so as to not form a pointed corner.

11. The method of claim 1, wherein forming the sheet further comprises forming at least one structural rib, the at least one structural rib extending along the width dimension between the two opposing sides, so as to contribute at least part of the spring force to hold open a vaginal canal for obstetric visualization and to urge the sheet to unroll or unfold to return to a native state.

12. The method of claim 11, wherein the at least part of the spring force comprises a first portion of the spring force to hold open a vaginal canal for obstetric visualization and to urge the sheet to unroll or unfold to return to a native state, and wherein the thickness of the flexible material of the sheet is to contribute a second portion of the spring force to hold open a vaginal canal for obstetric visualization and to urge the sheet to unroll or unfold to return to a native state, the first portion being greater than the second portion.

13. The method of claim 1, wherein the sheet has dimensions of no greater than seven centimeters between the two opposing ends along the length dimension, ten centimeters between the two opposing sides along the width dimension, and two millimeters between the two opposing sides along the height dimension.

14. The method of claim 1, wherein the two opposing sides are each planar in the native state.

15. A method comprising:
inserting a retractor vaginally, wherein the retractor comprises
a sheet of a flexible material, the flexible material comprising at least one of a rubber, plastic or silicone, wherein the sheet has two opposing sides along a width dimension, two opposing ends along a length dimension, and a height dimension, and
a flange at a first one of the two opposing ends, the flange extending between the two opposing sides, the flange providing a structure to grip the sheet, and to position and withdraw the sheet while in a deployed state, wherein the flange is raised along the height dimension relative to a first one of the two opposing sides and in a direction away from a second one of the two opposing sides, so as to provide a stop inhibiting vaginal insertion along the length dimension beyond a position dictated by the flange;
performing surgical repair of the vaginal tissue; and
withdrawing the retractor following said surgical repair;
wherein inserting the retractor comprises selectively rolling or folding the sheet so to urge the flexible material toward the deployed state, to provide a spring force to hold open a vaginal canal during vaginal insertion for obstetric visualization and to urge the sheet to unroll or unfold to return to a native state.

16. The method of claim 15, wherein the method further comprises trimming the sheet with scissors so as to reduce a size the retractor along at least one of the length or width dimensions.

17. A retractor for obstetric use, the retractor comprising:
a sheet of a flexible material, the flexible material comprising at least one of a rubber, plastic or silicone, wherein the sheet has two opposing sides along a width dimension, two opposing ends along a length dimension, and a height dimension;
a flange at a first one of the two opposing ends, the flange extending between the two opposing sides, the flange providing a structure to grip the sheet, and to position and withdraw the sheet while in a deployed state, wherein the flange is raised along the height dimension relative to a first one of the two opposing sides and in a direction away from a second one of the two opposing sides, so as to provide a stop inhibiting vaginal insertion along the length dimension beyond a position dictated by the flange; and
wherein the flexible material and the flange are to permit the sheet to be selectively rolled or folded to urge the flexible material toward the deployed state, to provide a spring force to hold open a vaginal canal for obstetric visualization and to urge the sheet to unroll or unfold to return to a native state.

\* \* \* \* \*